(12) United States Patent
Gately

(10) Patent No.: US 7,959,675 B2
(45) Date of Patent: Jun. 14, 2011

(54) SPINE IMPLANT INSERTION DEVICE AND METHOD

(75) Inventor: Nicholas V. Gately, Lambertville, NJ (US)

(73) Assignee: G&L Consulting, LLC, New York, NY (US)

( * ) Notice: Subject to any disclaimer, the term of this patent is extended or adjusted under 35 U.S.C. 154(b) by 274 days.

(21) Appl. No.: 11/278,552

(22) Filed: Apr. 4, 2006

(65) Prior Publication Data

US 2006/0241761 A1    Oct. 26, 2006

Related U.S. Application Data

(60) Provisional application No. 60/669,356, filed on Apr. 8, 2005.

(51) Int. Cl.
*A61F 2/44* (2006.01)

(52) U.S. Cl. .................... 623/17.11; 623/17.16; 606/99; 606/249

(58) Field of Classification Search ............... 623/17.11, 623/17.12–17.16; 606/99, 246, 249, 914, 606/915, 916; 403/61, 113, 114, 115, 116
See application file for complete search history.

(56) References Cited

U.S. PATENT DOCUMENTS

| | | |
|---|---|---|
| 5,609,635 A | 3/1997 | Michelson |
| 5,653,763 A | 8/1997 | Errico et al. |
| 5,713,899 A | 2/1998 | Marnay et al. |
| 5,717,006 A | 2/1998 | Daculsi et al. |
| 5,895,428 A * | 4/1999 | Berry .......................... 623/17.15 |
| 6,143,032 A | 11/2000 | Schafer et al. |
| 6,143,033 A | 11/2000 | Paul et al. |
| 6,245,108 B1 | 6/2001 | Biscup |
| 6,346,123 B1 | 2/2002 | McKay |
| 6,478,800 B1 * | 11/2002 | Fraser et al. ..................... 606/99 |
| 6,517,544 B1 | 2/2003 | Michelson |
| 6,537,589 B1 | 3/2003 | Chae et al. |
| 6,558,424 B2 * | 5/2003 | Thalgott ..................... 623/17.16 |
| 6,599,294 B2 | 7/2003 | Fuss et al. |
| 6,682,534 B2 | 1/2004 | Patel et al. |
| 6,719,794 B2 | 4/2004 | Gerber et al. |
| 7,018,413 B2 * | 3/2006 | Kruger ......................... 623/17.11 |
| 7,105,023 B2 * | 9/2006 | Eckman ..................... 623/17.11 |
| 7,226,483 B2 | 6/2007 | Gerber et al. |
| 7,235,082 B2 * | 6/2007 | Bartish et al. ................... 606/99 |
| 7,338,526 B2 | 3/2008 | Steinberg |

(Continued)

FOREIGN PATENT DOCUMENTS

WO    WO 98/56319    12/1998

(Continued)

OTHER PUBLICATIONS

PCT/US2004/023721 (PCT International Search Report)—completed Nov. 23, 2004.

(Continued)

*Primary Examiner* — Eduardo C Robert
*Assistant Examiner* — Jan Christopher Merene
(74) *Attorney, Agent, or Firm* — Nixon & Vanderhye P.C.

(57) ABSTRACT

A spinal implant include a top, wherein at least a portion of the top is configured to contact a first vertebra, a bottom, wherein at least a portion of the bottom is configured to contact a second vertebra, a side having a releasable attachment to receive an insertion device and a cam surface to engage a cam on the insertion device.

26 Claims, 4 Drawing Sheets

U.S. PATENT DOCUMENTS

| | | | |
|---|---|---|---|
| 2002/0107573 A1 | 8/2002 | Steinberg | |
| 2002/0161444 A1* | 10/2002 | Choi | 623/17.11 |
| 2003/0100950 A1 | 5/2003 | Moret | |
| 2003/0135276 A1* | 7/2003 | Eckman | 623/17.11 |
| 2004/0153065 A1* | 8/2004 | Lim | 606/53 |
| 2004/0193159 A1 | 9/2004 | Zucherman et al. | |
| 2005/0004671 A1 | 1/2005 | Ross et al. | |
| 2005/0027360 A1 | 2/2005 | Webb et al. | |
| 2005/0096745 A1* | 5/2005 | Andre et al. | 623/17.11 |
| 2005/0256578 A1 | 11/2005 | Blatt et al. | |
| 2005/0283245 A1 | 12/2005 | Gordon et al. | |
| 2006/0129244 A1 | 6/2006 | Ensign | |
| 2006/0229627 A1 | 10/2006 | Hunt et al. | |
| 2006/0235426 A1* | 10/2006 | Lim et al. | 606/99 |
| 2006/0241642 A1 | 10/2006 | Arnin et al. | |
| 2007/0093850 A1 | 4/2007 | Harris et al. | |
| 2007/0208343 A1 | 9/2007 | Magerl et al. | |
| 2007/0225726 A1* | 9/2007 | Dye et al. | 606/99 |
| 2007/0225805 A1 | 9/2007 | Schmieding | |
| 2007/0282449 A1 | 12/2007 | de Villiers et al. | |
| 2008/0009880 A1* | 1/2008 | Warnick et al. | 606/99 |
| 2008/0027544 A1 | 1/2008 | Melkent | |
| 2008/0097454 A1 | 4/2008 | De Ridder et al. | |
| 2008/0109005 A1 | 5/2008 | Trudeau et al. | |
| 2008/0125865 A1 | 5/2008 | Abdelgany | |
| 2009/0054991 A1* | 2/2009 | Biyani et al. | 623/17.16 |
| 2009/0276049 A1* | 11/2009 | Weiland | 623/17.16 |
| 2010/0094422 A1* | 4/2010 | Hansell et al. | 623/17.16 |
| 2010/0256760 A1* | 10/2010 | Hansell | 623/17.11 |

FOREIGN PATENT DOCUMENTS

| | | |
|---|---|---|
| WO | WO 02/17823 | 3/2002 |
| WO | 2006079356 | 8/2006 |

OTHER PUBLICATIONS

U.S. Appl. No. 11/870,844, filed Oct. 11, 2007.
U.S. Appl. No. 11/000,265, filed Dec. 11, 2007.
In U.S. Appl. No. 11/870,844, Office Action mailed Nov. 9, 2010.

* cited by examiner

SPINE IMPLANT INSERTION DEVICE AND METHOD

This application claims the benefit of U.S. Provisional Patent Application Ser. No. 60/669,356 filed Apr. 8, 2006, which is incorporated by reference.

BACKGROUND OF THE INVENTION

The present invention generally relates to the field of medical devices. Some embodiments of the invention relate to spinal implants inserted in the spine of a patient during surgical procedures and to instruments used to insert the implants. Other embodiments of the invention relate to methods for positioning, rotating and advancing an implant during a surgical procedure.

A spinal implant may be used to stabilize a portion of a spine. The implant may promote bone growth between adjacent vertebra that fuses the vertebra together. The implant may include a spherical protrusion, a threaded pin and an angled surface to facilitate remote adjustment of the implant position using an insertion instrument.

The insertion instrument may include, but is not limited to, a threaded rod, an actuator and a lock knob. The insertion instrument can be attached and detached to the implant, rotate the implant by transferring torque from the actuator to the implant. The actuator can be used to lock the implant in relation to the instrument. The rod can be used to apply force to the implant and advance it. The implant and instruments may be supplied in an instrument kit.

An intervertebral disc may degenerate. Degeneration may be caused by trauma, disease, and/or aging. An intervertebral disc that becomes degenerated may have to be partially or fully removed from a spinal column. Partial or full removal of an intervertebral disc may destabilize the spinal column. Destabilization of a spinal column may result in alteration of a natural separation distance between adjacent vertebra. Maintaining the natural separation between vertebra may prevent pressure from being applied to nerves that pass between vertebral bodies. Excessive pressure applied to the nerves may cause pain and nerve damage.

During a spinal fixation procedure, a spinal implant may be inserted in a space created by the removal or partial removal of an intervertebral disc between adjacent vertebra. The spinal implant may maintain the height of the spine and restore stability to the spine. Bone growth may fuse the implant to adjacent vertebra.

A spinal implant may be inserted during a spinal fixation procedure using an anterior, lateral, posterior, or transverse spinal approach. A discectomy may be performed to remove or partially remove a defective or damaged intervertebral disc. The discectomy may create a space for a spinal implant. The amount of removed disc material may correspond to the size and type of spinal implant to be inserted.

Spinal implants are described in U.S. Pat. No. 5,653,763 to Errico et al.; U.S. Pat. No. 5,713,899 to Marney et al.; U.S. Pat. No. 6,143,033 to Paul et al.; U.S. Pat. No. 6,245,108 to Biscup; and U.S. Pat. No. 5,609,635 to Michelson, United States Patent Application 20050027360 to Webb.

BRIEF DESCRIPTION OF THE INVENTION

A spinal implant is disclosed comprising: a top, wherein at least a portion of the top is configured to contact a first vertebra; a bottom, wherein at least a portion of the bottom is configured to contact a second vertebra and a side having a releasable attachment to receive an insertion device and a cam surface to engage a cam on the insertion device. The spinal implant may include a hemispherical mount and a pin mounted within the spinal implant, wherein the insertion device attaches to the pin that serves as an axis of rotation and pivots around the pin with respect to the hemispherical housing.

A method is disclose comprising: inserting an implant between portions of bone, wherein the implant locked at a first angle relative to a shaft of the instrument; loosening the implant relative to the shaft; turning the shaft to pivot the implant relative to the shaft, and releasing the implant from the instrument so that the implant is in position between the bone. Turning the shaft rotates a cam fixed to the shaft across a cam surface on the implant, wherein the cam surface is slanted and the movement of the cam across the cam surface pivots the implant.

DETAILED DESCRIPTION OF THE INVENTION

Figure 1:
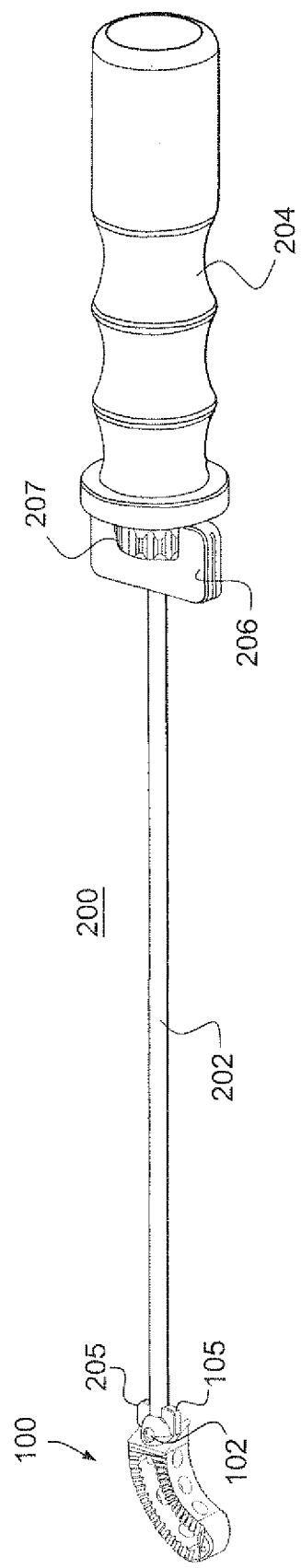
FIG. 1 is a top-side perspective view of a spinal implant attached to an insertion instrument.

FIG. 1 shows the spinal implant 100 releasably attached to an insertion instrument 200. The implant 100 may be made by made of PEEK plastic commonly used in spinal implants. The implant includes a hemispherical mount 105 and slanted cam surface 106 from which the mount protrudes. The tip of rod 201 pivotably attaches to the mount such that the implant may pivot with respect to the axis of the instrument. The pivoting of the implant is controlled by the a knob on the instrument that rotates the cam wings 205 about the hemispherical surface. The rotation of the cam, slides the front edges of the cam wings across the and cam surface 106 and thereby forces the implant to pivot with respect to the axis of the instrument.

A knob (e.g. actuator wings) 206 on the on the proximal end of the instrument enables a surgeon to rotate the cam and thereby adjust the angle between the implant and the axis of the instrument. Pivoting of the implant is caused as the actuator pushers 205 (e.g., cam) act on the slanted surface 106 of the implant 100. As the cammed actuator 202 rotate and slide across the slanted surface 106, the implant makes a yaw movement with respect to the axis of the instrument. Actuator 202 is equipped with the actuator wings 206 used to rotate pushers 205 (cam) from outside of the patient's body.

Locking knob 207 may be tightened to bind the actuator against the implant effectively locking the implant with respect to the instrument. When locked, axial force and torque can be applied to the handle 204 to advance the implant into the spinal space and position the implant in the space. Turning the locking knob 207 that is threaded inside and engages threads on the proximal end of the rod causes the actuator 202 that is hollow to slide axially forward over the threaded rod 201 and thereby loosen or tighten the actuator against the implant.

Figure 2:
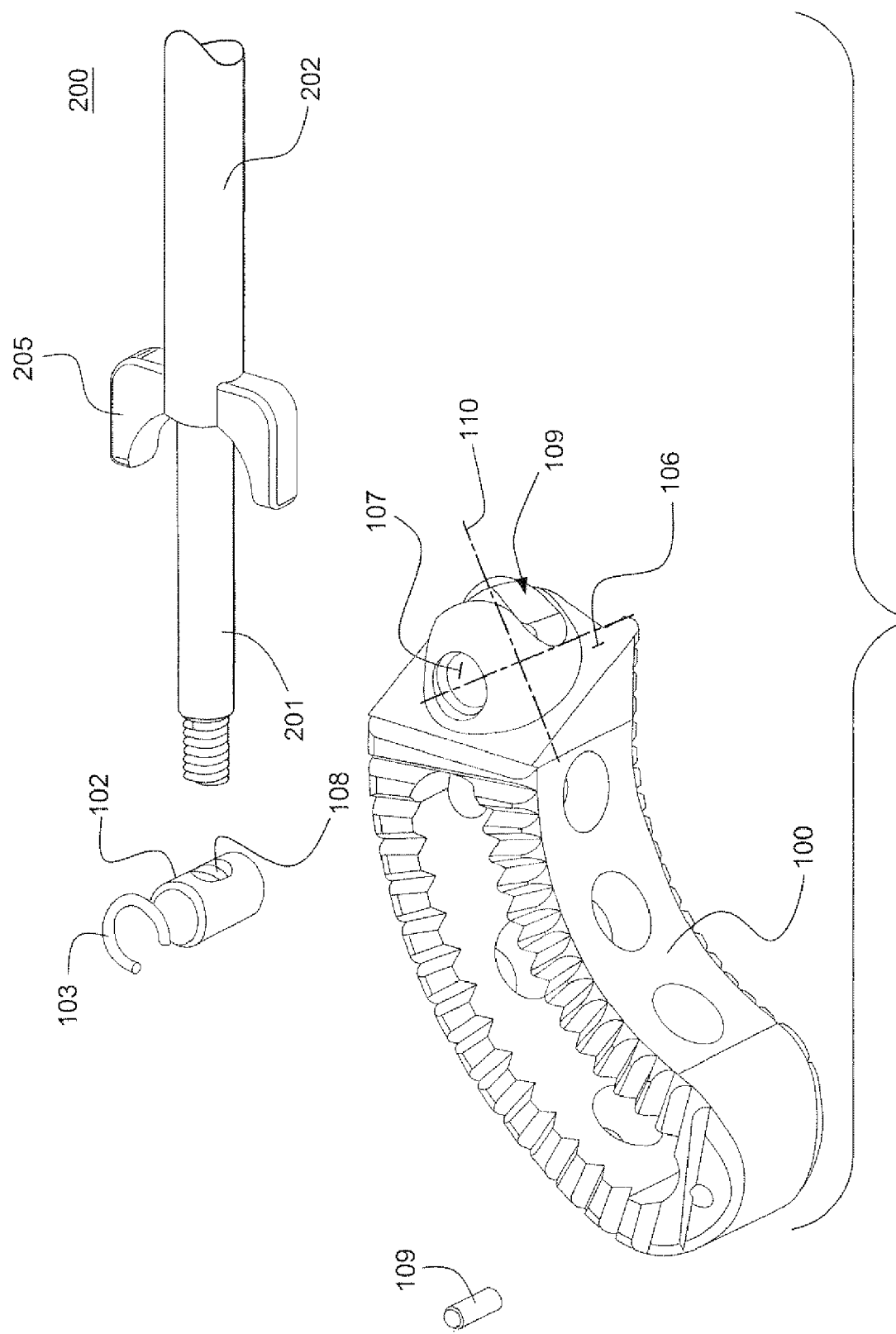
FIG. 2 is an exploded view showing the spinal implant separate from the insertion instrument.

FIG. 2 shows the details of the attachment of the implant 100 to the instrument 200. Threaded pin 102 is inserted into the channel 107 in the spherical protrusion (mount) 105 and retained there by a snap ring 103. Coordinate axes 110 illustrate the curvature in orthogonal directions of the surface of the spherical protrusion. A threaded hollow shaft 108 in the threaded pin 102 is aligned with the slot opening 109 of the implant so that the treaded rod 201 can be threaded into the shaft 108 of the pin 102. Slot opening allows pivoting of the implant by accommodating the pendulum motion of the rod 201. Pin 104 is made of a material that enhances X-ray imaging. Making the pin visible assists the physician in the positioning of the implant while viewing a real-time x-ray image of the implant and vertebra.

The actuator 202 may be a hollow tube that is coaxial with the rod 201. The pushers are fixed to the distal end of the actuator. The pushers 205 include cams that engage a cam surface 106 on the implant. The proximal end of the tube has a knob (e.g. actuator wings) 206 to turn the tube and thereby move the cams against the cam surface. The angle of the implant with respect to the implant is adjusted by moving the cam against the cam surface. Adjusting the angle may allow the surgeon to properly place the implant in the spine area.

Figure 3:
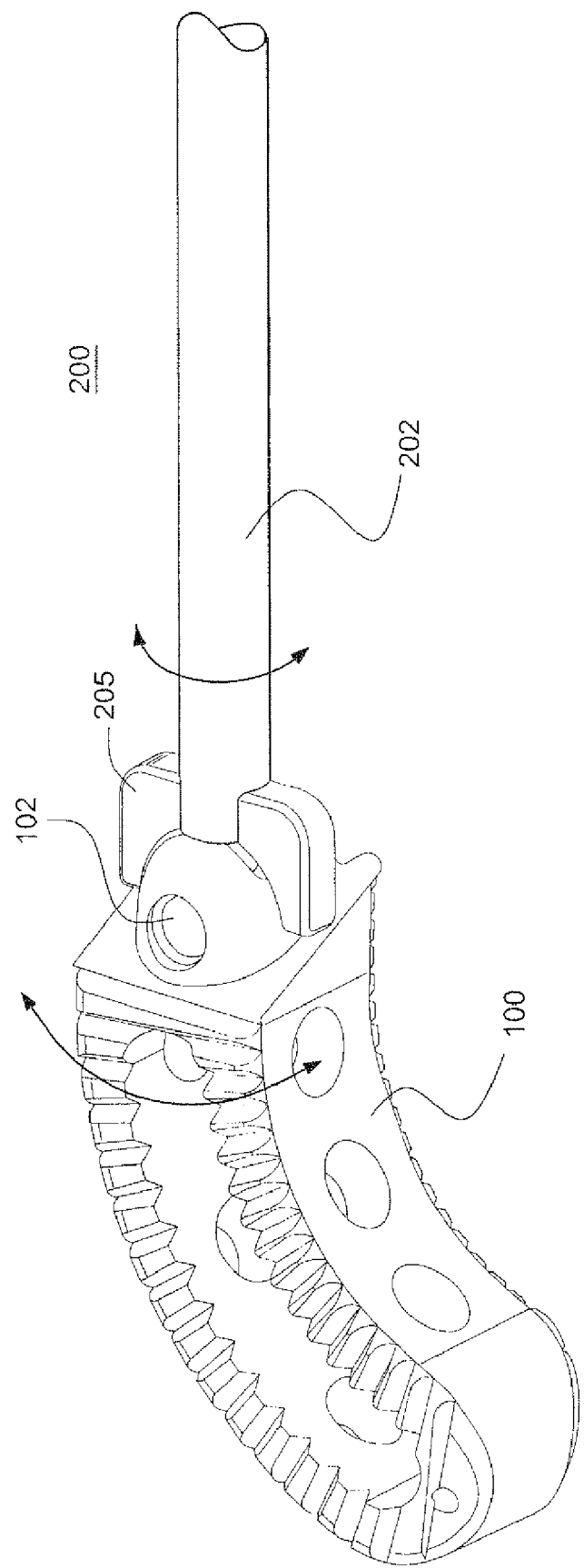
FIG. 3 is a perspective view of the FIG. 3 illustrates the interaction between the Actuator 202 of the instrument and the implant 100.

FIG. 3 illustrates the interaction between the Actuator 202 of the instrument and the implant 100. The actuator 202 is rotated around the axis of the threaded rod 201 that is engaged in the threaded pin 102. As the cammed pushers 205 rotate, they push against the surface 106. As a result the implant 100 turns around the axis of the pin 102. It can be envisioned as if the implant is performing a "dog wagging its tail" motion with respect to the insert instrument 200.

If the locking knob 207 (FIG. 1) is rotated, the actuator 202 is pushed against the implant 100. Both pushers are advanced towards the surface 106 to bind the actuator against the implant so as to lock the implant with respect to the instrument. When locked, the assembly of the implant and instrument can be advanced while retaining the desired angle of the implant 100 in relation to the insertion instrument 200.

Figure 4:
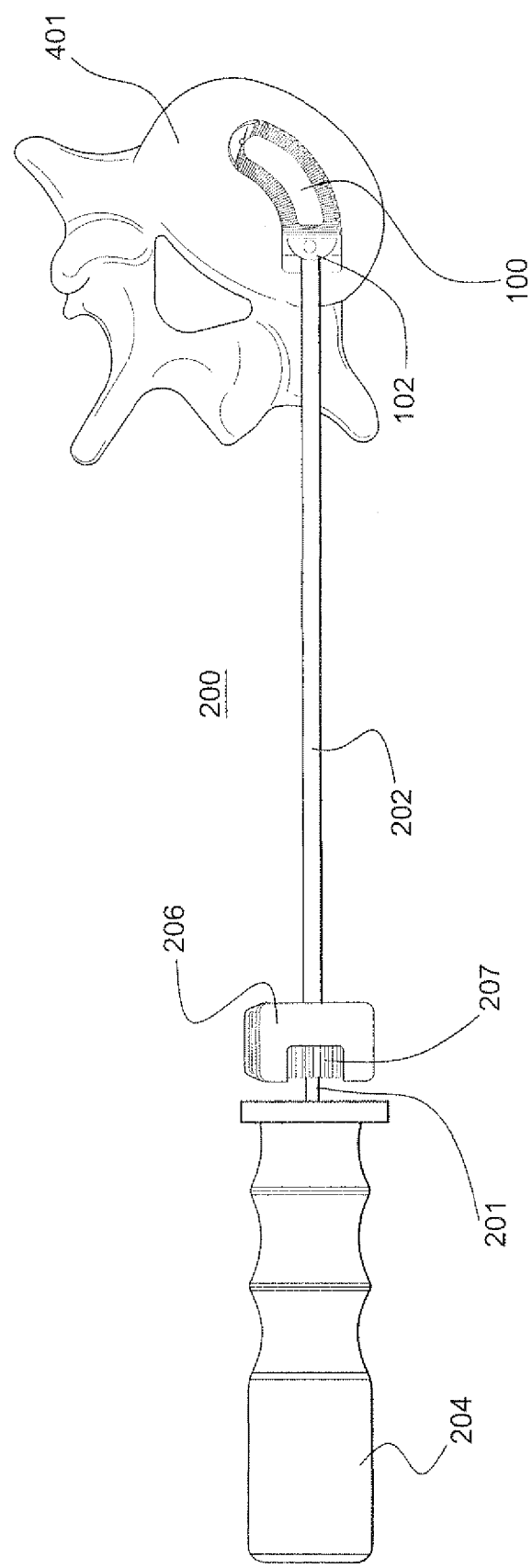
FIG. 4 is a perspective view of the implant releasably attached to the insertion instrument and positioned over a vertebra.

FIG. 4 shows the implant 100 with the insertion instrument 200 attached and in position on a patient vertebra 401. Rotation of the actuator 202 in relation to the axis of the threaded rod 201 results in the rotation of the implant 100 around the axis of the pin 102. Rotation of the knob 207 pushes the actuator 202 into the implant locking the assembly. When the assembly is locked hammer tapping can be applied to the handle 204 to advance the assembly forward.

A spinal implant may be used to stabilize a portion of a spine. The implant may promote bone growth between adjacent vertebra that fuses the vertebra together. An implant may include an opening through a height of a body of the implant. The body of the implant may include curved sides. A top and/or a bottom of the implant may include protrusions that contact and/or engage vertebral surfaces to prevent backout of the implant from the disc space.

A spinal implant may be used to provide stability and promote fusion of adjacent vertebra. The implant may be used in conjunction with a spinal stabilization device such as a bone plate or rod-and-fastener stabilization system. The implant may establish a desired separation distance between vertebra. The implant may promote bone growth between adjacent vertebra that fuses the vertebra together. Instrument at is necessary for insertion of an implant in a patient and alignment of the implant in the space.

A discectomy may be performed to establish a disc space between vertebra. The disc space may be prepared for implant insertion by distraction of adjacent vertebra, rasping and filing of the bone to achieve the desired spacing.

It is desired to perform insertion of the implant and positioning of the implant using minimum number of inserted instruments and thought the smallest possible insertion channel in the body.

Implants may be constructed of biocompatible materials sufficiently strong to maintain spinal distraction. Implants may include, but are not limited to, allograft bone, xenograft bone, autograft bone, metals, ceramics, inorganic compositions, polymers such as PEEK, or combinations thereof. If the implant is not made of bone, surfaces of the implant that contact bone may be treated to promote fusion of the implant to the bone. Treatment may include, but is not limited to, applying a hydroxyapatite coating on contact surfaces, spraying a titanium plasma on contact surfaces, and/or texturing the contact surfaces by scoring, peening, implanting particles in the surfaces, or otherwise roughening the surfaces.

In some embodiments, an implant may include an opening that extends through a body of the implant. The opening may have a regular shape or an irregular shape. Bone graft may be placed in the opening. The bone graft may be autogenic bone graft, allogenic bone graft, xenogenic bone graft, and/or synthetic bone graft. Some implant embodiments may be constructed from allogenic bone, such as cortical bone from a femur, tibia, or other large bone. In some embodiments, an implant may be formed from one or more pieces of allograft bone cut to a desired shape.

In certain embodiments, sides of an implant may be shaped to increase contact between an implant and adjacent vertebra with notches, ribs and other similar features. Increasing contact of an implant with adjacent vertebra may inhibit movement of the implant after insertion. An increased contact area between an implant and adjacent vertebra may promote bone growth between adjacent vertebra.

In some embodiments, one or more sides of an implant may be curved. One or more curved sides of an implant may allow the implant to be maneuvered in a disc space during insertion of the implant. The curvature of a side may approximate a curvature of an anterior side of a vertebra adjacent to which the implant is inserted.

Instruments may be used to prepare a space for an implant between adjacent vertebra. An instrument may be used to insert an implant in a prepared space. Instruments may be supplied to a surgeon or surgical team in an instrument set. An instrument set may include one or more implants for use during an insertion procedure. An instrument set may include implants of various sizes and/or lordotic angles to allow selection of an implant to suit a patient during surgery. Instrument is attached to the implant before the insertion into the body. When the desired position of the implant is achieved, instrument is disengaged from the implant and can be extracted from the body.

An instrument acts as an implant inserter. The implant inserter may be used to push the implant and to rotate the implant. After insertion of the implant, the implant may be released from the inserter without the application of significant repositioning forces to the implant. It can be imagined that the insertion instrument can be screwed into the implant using threads or use other techniques such as a tightening collet, jamming or grabbing. In the disclosed embodiment the implant turns around the axis of the implant pin as a result of the rotation of cam pushers. It can be imagined that other mechanisms can be used to rotate the implant such as ratchets or threaded push rods. The implant inserter may have a low profile that allows for visualization of the implant and surrounding area during insertion of the implant. Implant is equipped to couple and uncouple from the instrument.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A spinal implant comprising:
   a top, wherein at least a portion of the top is configured to contact a first vertebra;
   a bottom, wherein at least a portion of the bottom is configured to contact a second vertebra;
   a curved surface on a side of the spinal implant between the top and bottom, wherein the curved surface is curved along orthogonal directions, wherein all points on the curved surface are at a common radius from a center of the curved surface;
   a pivot pin in the spinal implant and accessible through a slot in the curved surface, wherein a longitudinal axis of the pivot pin is parallel to one of the orthogonal directions, and
   a bearing surface on the side of the body and directly adjacent the curved surface, and the bearing surface is linear.

2. The spinal implant in claim 1 wherein a pivot axis of the spinal implant is coaxial to the pivot pin.

3. The spinal implant in claim 2 wherein the pivot axis extends through the top and bottom of the spinal implant.

4. The spinal implant in claim 1 wherein the curved surface is at least partially hemispherical.

5. The spinal implant in claim 2 wherein the pivot pin includes a threaded hole extending perpendicular to the pivot axis and accessible through the slot.

6. The spinal implant in claim 1 wherein the implant pivots about the pivot pin.

7. The spinal implant of claim 1 wherein the curved surface includes an aperture to receive the pivot pin.

8. The spinal implant of claim 1 further comprising a slanted surface on the side of the spinal implant and adjacent the curved surface, wherein the slanted surface engages rotatable fingers at a distal end of a shaft of an insertion tool for inserting the spinal implant in a spine.

9. The spinal implant of claim 1 further comprising a bearing surface on the side of the spinal implant and adjacent opposites sides of the curved surface, wherein the bearing surface engages a rotating distal end of a shaft of an insertion tool for inserting the spinal implant in a spine, wherein at least one of the bearing surface and the distal end include a surface slanted with respect to a longitudinal axis of the shaft.

10. A spinal implant comprising:
    a top, wherein at least a portion of the top is configured to contact a first vertebra;
    a bottom, wherein at least a portion of the bottom is configured to contact a second vertebra;
    a side of the spinal implant, wherein the side is at an end of the implant and is between the top and the bottom;
    a hemispherical housing protruding from the side of the spinal implant;
    a pin mounted within the housing, wherein the pin is accessible through a slot in the housing and the pin is perpendicular to the slot and perpendicular to the top and bottom of the implant, and
    a bearing surface on the side of the body and directly adjacent the housing and the bearing surface is linear.

11. The spinal implant of claim 1 wherein the pin includes a threaded aperture.

12. A method comprising:
    providing a spinal implant, wherein the spinal implant includes a top, bottom and a side extending from the top and the bottom, the side includes a protruding hemispherical housing and a bearing surface directly adjacent the curved surface, wherein the bearing surface is linear in a direction extending through the hemispherical surface,
    inserting the spinal implant into the spine using an instrument such that the top and bottom of the implant abut adjacent vertebra of the spine, wherein the implant is initially locked at a first angle relative to a shaft of the instrument by binding a cam surface on the end of the shaft against the bearing surface of the implant;
    loosening the implant relative to the shaft to allow the cam surface to turn against the bearing surface;
    turning the shaft while the implant is between the vertebra and after the loosening of the implant, wherein the turning of the shaft rotates the cam surface against the bearing surface to pivot the implant with respect to the shaft, and
    releasing the implant from the instrument so that the implant is between the vertebra.

13. The method of claim 12 wherein the turning of the shaft to rotate the cam surface slides the cam surface across the bearing surface on the implant.

14. The method of claim 12 wherein the bearing surface is a slanted planar surface and the movement of the cam surface across the bearing surface is an arc shaped movement.

15. A spinal implant comprising:
    a first surface configured to contact a first vertebra;
    a second surface, opposite to the first surface, configured to contact a second vertebra, and
    a side of the spinal implant having a convex surface curved along two orthogonal directions, wherein the convex surface extends a majority of the side along a direction extending between the first surface and the second surface and all points on the convex surface are a common radius from a center of the convex surface;
    a pivot pin mounted in a chamber of the implant and the pivot pin having a aperture accessible through a channel in the convex surface, wherein a longitudinal axis of the pivot pin is parallel to one of the orthogonal directions and wherein the aperture provides a releasable connection, and
    a bearing surface protruding from the side of the spinal implant and directly adjacent the convex surface, wherein the bearing surface is linear.

16. The spinal implant of claim 15 wherein the pivot pin is perpendicular to the channel.

17. The spinal implant of claim 15 wherein the channel is perpendicular to the pivot pin and parallel to the first and second surfaces of the implant.

18. The spinal implant of claim 15 wherein the convex surface includes an aperture to receive the pivot pin.

19. The spinal implant of claim 15 wherein the convex surface is partially hemispherical.

20. The spinal implant of claim wherein the bearing surface is a cam planar surface slanted with respect to the pivot axis and the longitudinal axis.

21. The spinal implant of claim 15 wherein the aperture is threaded.

22. A spinal implant for spinal bone fusion comprising:
    a body including a top surface adapted to engage a first vertebra and a bottom surface adapted to engage a second vertebra, where the second vertebra is separated from the first vertebra by the spinal implant;

a side of the body between the top surface and the bottom surface;

a housing protruding from the side of the body, wherein the housing has an outer surface curved in orthogonal directions, wherein all points on the outer surface are at a common radius from a center of the outer surface, and the outer surface is curved along a width of the housing in a direction extending at least partially between the top surface and the bottom surface;

a pivotable pin mounted within the housing and the pin being parallel to one of the orthogonal directions, and a slot in the outer surface of the housing exposes the pin, and a bearing surface on the side of the body and directly adjacent the housing, wherein the bearing surface is linear.

23. The spinal implant of claim 22 wherein the pin comprises a threaded orifice exposed by a channel in the housing.

24. The spinal implant of claim 23 wherein the slot is perpendicular to the pin.

25. The spinal implant of claim 22 wherein the outer surface of the housing curves in a dimension parallel to the top and bottom surfaces.

26. The spinal implant of claim 22 wherein the pivotable pin is perpendicular to the top and bottom surfaces.

* * * * *